United States Patent
Funderburk et al.

(10) Patent No.: US 9,907,966 B2
(45) Date of Patent: Mar. 6, 2018

(54) IMPLANTABLE MEDICAL DEVICE FOR PROVIDING STIMULATION THERAPY

(71) Applicant: Boston Scientific Neuromodulation Corporation, Valencia, CA (US)

(72) Inventors: Jeffery V. Funderburk, Stevenson Ranch, CA (US); Randy L. Brase, Castaic, CA (US); Robert R. Tong, Valencia, CA (US); Md. Mizanur Rahman, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/442,324

(22) Filed: Feb. 24, 2017

(65) Prior Publication Data

US 2017/0157406 A1 Jun. 8, 2017

Related U.S. Application Data

(63) Continuation of application No. 14/663,222, filed on Mar. 19, 2015, now Pat. No. 9,597,519, which is a
(Continued)

(51) Int. Cl.
*A61N 1/00* (2006.01)
*A61N 1/375* (2006.01)
(Continued)

(52) U.S. Cl.
CPC ....... *A61N 1/3754* (2013.01); *A61N 1/36125* (2013.01); *A61N 1/3787* (2013.01)

(58) Field of Classification Search
CPC .................................................. A61N 1/3754
(Continued)

(56) References Cited

U.S. PATENT DOCUMENTS

| 4,276,882 A | 7/1981 | Dickhudt et al. |
| 6,516,227 B1 * | 2/2003 | Meadows ............ A61N 1/0553 |
| | | 607/117 |

(Continued)

FOREIGN PATENT DOCUMENTS

| EP | 1832254 | 9/2009 |
| JP | 05-144494 | 6/1993 |

(Continued)

*Primary Examiner* — Nadia A Mahmood
(74) *Attorney, Agent, or Firm* — Lewis, Reese & Nesmith, PLLC

(57) ABSTRACT

An electrical stimulation system provides stimulation therapy to a patient. The system includes a neurostimulation lead that contacts patient tissue and couples with an implantable stimulation device, such as an implantable pulse generator, that receives stimulation parameters for providing stimulation therapy to a patient. The implantable stimulation device includes a header with a plurality of connector assemblies that receive an end of the neurostimulation lead, and a case containing a charging coil and a telemetry coil coupled to programming circuitry on a printed circuit board, which is in turn coupled to the connector assemblies via a feedthrough assembly. The telemetry coil receives data from an external programmer and transmits the data to the programming circuitry, which in turn uses the data to communicate to the connector assemblies and the neurostimulation lead to provide stimulation therapy to a patient.

20 Claims, 8 Drawing Sheets

Related U.S. Application Data continuation of application No. 14/251,488, filed on Apr. 11, 2014, now Pat. No. 8,989,864, which is a continuation of application No. 13/403,779, filed on Feb. 23, 2012, now Pat. No. 8,738,138.

(60) Provisional application No. 61/446,438, filed on Feb. 24, 2011.

(51) Int. Cl.
*A61N 1/36* (2006.01)
*A61N 1/378* (2006.01)

(58) Field of Classification Search
USPC .......................................................... 607/45
See application file for complete search history.

(56) References Cited

U.S. PATENT DOCUMENTS

| | | | |
|---|---|---|---|
| 6,895,280 B2 | 5/2005 | Meadows et al. | |
| 7,244,150 B1 | 7/2007 | Brase et al. | |
| 7,736,191 B1 * | 6/2010 | Sochor | A61N 1/3752 439/668 |
| 2005/0024837 A1 | 2/2005 | Youker et al. | |
| 2005/0131483 A1 | 6/2005 | Zhao et al. | |
| 2008/0071320 A1 | 3/2008 | Brase | |
| 2009/0018600 A1 | 1/2009 | Deininger et al. | |
| 2009/0024179 A1 | 1/2009 | Dronov | |
| 2010/0179618 A1 | 7/2010 | Marnfeldt et al. | |
| 2011/0112610 A1 | 5/2011 | Rahman et al. | |
| 2012/0053646 A1 | 3/2012 | Brase et al. | |
| 2014/0135882 A1 | 5/2014 | Prasannakumar et al. | |

FOREIGN PATENT DOCUMENTS

| | | |
|---|---|---|
| JP | 2002-263201 | 9/2002 |
| JP | 2004-146177 | 5/2004 |
| JP | 2008-053007 | 3/2008 |
| WO | 2006/104847 | 10/2006 |
| WO | 2009/117599 | 9/2009 |
| WO | 2010/035177 | 4/2010 |

* cited by examiner

IMPLANTABLE MEDICAL DEVICE FOR PROVIDING STIMULATION THERAPY

CROSS REFERENCE TO RELATED APPLICATIONS

The present application is a continuation of U.S. patent application Ser. No. 14/663,222, filed Mar. 19, 2015 (now allowed), which is a continuation of U.S. patent application Ser. No. 14/251,488, filed Apr. 11, 2014 (now U.S. Pat. No. 8,989,864), which is a continuation of U.S. patent application Ser. No. 13/403,779, filed Feb. 23, 2012 (now U.S. Pat. No. 8,738,138), which claims benefit to U.S. provisional patent application Ser. No. 61/446,438, filed Feb. 24, 2011, which applications are incorporated herein by reference.

FIELD OF THE INVENTION

The present invention relates to implantable medical devices, and more particularly, to devices and methods for providing stimulation therapy to patients.

BACKGROUND

Implantable stimulation devices generate and deliver electrical stimuli to bodily nerves and tissues for the therapy of various biological disorders, such as: pacemakers to treat cardiac arrhythmia; defibrillators to treat cardiac fibrillation; cochlear stimulators to treat deafness; retinal stimulators to treat blindness; muscle stimulators to produce coordinated limb movement; spinal cord stimulators to treat chronic pain; cortical and deep brain stimulators to treat motor and psychological disorders; and other neural stimulators to treat urinary incontinence, sleep apnea, shoulder sublaxation, etc. The present invention may find applicability in all such applications, although the description that follows will generally focus on the use of the invention within a spinal cord stimulation system, such as that disclosed in U.S. Pat. No. 6,516,227, issued Feb. 4, 2003 in the name of inventors Paul Meadows et al., which is incorporated herein by reference in its entirety.

Typical implantable stimulation devices include a neurostimulator, one or more leads electrically coupled to the neurostimulator, and an array of stimulator electrodes on each lead. The stimulator electrodes are in contact with or near the bodily tissue to be stimulated. A pulse generator in the neurostimulator generates electrical pulses that are delivered by the electrodes to bodily tissue. The neurostimulator typically includes an implantable rounded case having circuitry such as a printed circuit board, a telemetry coil for communicating with an external programmer to control the electrical pulses, and a charging coil for charging the neurostimulator.

The neurostimulator also includes a header having one or more connector assemblies for receiving the leads, wherein the connector assemblies have one or more connector contacts for coupling to the leads. In common models of such neurostimulators, there are two connector assemblies in the header, each having eight contacts. However, to allow for greater range in stimulation parameters, it is desirable for the header to include more electrode contacts for coupling to the lead, for example, thirty-two contacts. At the same time, it is preferred to keep the case and header as small as possible and to maintain a curved configuration for patient comfort. Therefore, a proper neurostimulator design to accommodate thirty-two electrodes, without affecting device performance, is desirable.

It is also common for neurostimulators to house a telemetry coil in the header. However, this requires a feedthrough to couple the telemetry coil to resonant circuit components and transceiver circuitry in the case. This can add to the complexity of the device and lead to problems with hermeticity. Additionally, the feedthroughs require significant extra steps during manufacture, thus allowing for greater error and quality concerns.

Another disadvantage of having the telemetry coil in the header is that the coil and the feedthroughs connected to the coil take up space in the header, which may be limited based on the complexity of the stimulation system. At the same time, it is desirable to make stimulation devices smaller for patient comfort. Moreover, while previous neurostimulators had eight or sixteen contacts for coupling to the electrode leads, newer designs may include thirty-two or more contacts, further limiting space in the header.

Thus, there remains a need for improved stimulation devices and methods that optimize performance with an increased number of electrodes and selective positioning of the telemetry coil, while also having a small, rounded configuration for patient comfort that does not compromise device performance.

SUMMARY

In accordance with one aspect of the present invention, a tissue stimulation system is provided. The stimulation system has at least one implantable neurostimulation lead and an implantable neurostimulator. The neurostimulator includes at least one connector assembly configured for respectively receiving the at least one neurostimulation lead, a case, a circuit board positioned in the case, a telemetry coil positioned in the case that is electrically coupled to the circuit board and spaced a distance away from the circuit board, and a charging coil positioned in the case that is electrically coupled to the circuit board. In one embodiment, the telemetry coil is positioned on a spacer that spaces the telemetry coil the distance away from the circuit board. In a further embodiment, a plurality of pins are affixed to the spacer, wherein at least one of the pins electrically couples the telemetry coil to the circuit board, and at least one of the pins mechanically couples the telemetry coil to the circuit board.

In a second aspect of the present invention, an implantable neurostimulator is provided. The neurostimulator has a case, a circuit board positioned in the case, a telemetry coil positioned in the case that is electrically coupled to the circuit board and spaced a distance away from the circuit board, and a charging coil positioned in the case that is electrically coupled to the circuit board. In one embodiment, the telemetry coil is positioned on a spacer that spaces the telemetry coil the distance away from the circuit board. In a further embodiment, a plurality of pins are affixed to the spacer, wherein at least one of the pins electrically couples the telemetry coil to the circuit board, and at least one of the pins mechanically couples the telemetry coil to the circuit board.

In a third aspect of the present invention, a tissue stimulation system is provided that includes at least one implantable neurostimulation lead and an implantable neurostimulator. The neurostimulator has a header with at least one connector assembly configured for respectively receiving the at least one neurostimulation lead, a circuit board having programming circuitry, and a flex circuit coupled between the at least one connector assembly and the circuit board. In one embodiment, the system includes a feedthrough assembly with a plurality of pins coupled to the flex circuit that electrically couple the flex circuit to the at least one connector assembly. In another embodiment, one or more of the plurality of pins traverse through one or more holes in the flex circuit. In another embodiment, the feedthrough assembly has a metal flange forming a well containing an insulative material, and the pins extend from the flex circuit through the insulative material. In yet another embodiment, the at least one connector assembly has a plurality of connector contacts for electrically coupling with the neurostimulation lead, and the pins are electrically coupled to the connector contacts.

In a fourth aspect of the present invention, an implantable neurostimulator is provided. The neurostimulator has at least one connector assembly configured for receiving at least one neurostimulation lead, a circuit board having programming circuitry, and a flex circuit coupled between the at least one connector assembly and the circuit board. In one embodiment, the system includes a feedthrough assembly with a plurality of pins coupled to the flex circuit that electrically couple the flex circuit to the at least one connector assembly. In another embodiment, one or more of the plurality of pins traverse through one or more holes in the flex circuit. In another embodiment, the feedthrough assembly has a metal flange forming a well containing an insulative material, and the pins extend from the flex circuit through the insulative material. In yet another embodiment, the at least one connector assembly has a plurality of connector contacts for electrically coupling with the neurostimulation lead, and the pins are electrically coupled to the connector contacts.

In a fifth aspect of the present invention, a tissue stimulation system is provided that includes at least one implantable neurostimulation lead and an implantable neurostimulator. The neurostimulator has at least one connector assembly configured for respectively receiving the at least one neurostimulation lead, a fastener configured for securing the respective one of the at least one neurostimulation leads in the at least one connector assembly, and at least one septum, each having an outer block and an inner block framed within the outer block. Adjacent edges of the inner and outer blocks form at least one slot for receiving a tool for manipulating the fastener for securing the respective one of the at least one neurostimulation leads in the respective one of the at least one connector assembly. In one embodiment, the neurostimulator has a retainer in which the at least one connector assembly is positioned. In another embodiment, a connector block is coupled to each at least one connector assembly and has the fastener positioned therein. In another embodiment, the outer and inner blocks of the at least one septum are composed of silicone.

In yet another embodiment, the neurostimulator has a shell housing the at least one connector assembly, and the shell has a first transverse line and a second transverse line both aligned parallel to the at least one connector assembly. The first transverse line extends between first opposing ends of the shell, the second transverse line extends between second opposing ends of the shell, and the first transverse line is shorter than the second transverse line. In a further embodiment, at least one upper connector assembly longitudinally aligned along the first transverse line, and at least one lower connector assembly longitudinally aligned along the second transverse line. In yet a further embodiment, the neurostimulator has at least one upper strain relief member longitudinally aligned along the first transverse line and extending between an end of the at least one upper connector assembly and one of the first opposing ends of the shell, and at least one lower strain relief member longitudinally aligned along the second transverse line and extending between an end of the at least one lower connector assembly and one of the second opposing ends of the shell. The at least one upper strain relief member has a shorter length than the at least one lower strain relief member.

In a sixth aspect of the present invention, an implantable neurostimulator is provided. The neurostimulator has at least one connector assembly configured for receiving a neurostimulation lead, a fastener configured for securing the respective one of the at least one neurostimulation leads in the at least one connector assembly, and at least one septum, each having an outer block and an inner block framed within the outer block. Adjacent edges of the inner and outer blocks form at least one slot for receiving a tool for manipulating the fastener for securing the respective one of the at least one neurostimulation leads in the respective one of the at least one connector assembly. In one embodiment, the neurostimulator has a retainer in which the at least one connector assembly is positioned. In another embodiment, a connector block is coupled to each at least one connector assembly and has the fastener positioned therein. In another embodiment, the outer and inner blocks of the at least one septum are composed of silicone.

In yet another embodiment, the neurostimulator has a shell housing the at least one connector assembly, and the shell has a first transverse line and a second transverse line both aligned parallel to the at least one connector assembly. The first transverse line extends between first opposing ends of the shell, the second transverse line extends between second opposing ends of the shell, and the first transverse line is shorter than the second transverse line. In a further embodiment, at least one upper connector assembly longitudinally aligned along the first transverse line, and at least one lower connector assembly longitudinally aligned along the second transverse line. In yet a further embodiment, the neurostimulator has at least one upper strain relief member longitudinally aligned along the first transverse line and extending between an end of the at least one upper connector assembly and one of the first opposing ends of the shell, and at least one lower strain relief member longitudinally aligned along the second transverse line and extending between an end of the at least one lower connector assembly and one of the second opposing ends of the shell. The at least one upper strain relief member has a shorter length than the at least one lower strain relief member.

In a seventh aspect of the present invention, an implantable neurostimulator is provided. The neurostimulator has a connector header configured for receiving a neurostimulation lead, a divot formed in each of the opposing sides of the connector header, and a suture hole extending between the divots. In one embodiment, each divot has a plurality of side surfaces, and each side surface is angled less than 90 degrees from an outer surface of the connector header. In another embodiment, each divot has a bottom surface, and a terminating end of the suture hole is positioned at the bottom surface.

In an eighth aspect of the invention, an implantable neurostimulator is provided. The neurostimulator has a shell having a first transverse line extending between first opposing ends of the shell, and a second transverse line extending between second opposing ends of the shell, wherein the first transverse line is shorter than the second transverse line. The neurostimulator also has at least one upper connector assembly and at least one lower connector assembly housed in the shell, each configured for receiving a neurostimulator lead, wherein the at least one upper connector assembly is longitudinally aligned along the first transverse line, and the at least one lower connector assembly is longitudinally aligned along the second transverse line. The neurostimulator also has at least one upper strain relief member longitudinally aligned along the first transverse line and extending between an end of the at least one upper connector assembly and one of the first opposing ends of the shell, and at least one lower strain relief member longitudinally aligned along the second transverse line and extending between an end of the at least one lower connector assembly and one of the second opposing ends of the shell. The at least one upper strain relief member has a shorter length than the at least one lower strain relief member.

In one embodiment, the at least one upper connector assembly and at least one lower connector assembly has contacts for electrically coupling to the respective electrode lead received therein. In another embodiment, the at least one upper connector assembly and at least one lower connector assembly are positioned in a retainer. In yet another embodiment, the neurostimulator has at least one upper connector block adjacent the at least one upper connector assembly and at least one lower connector block adjacent the at least one lower connector assembly. In yet another embodiment, each of the at least one upper connector block and at least one lower connector block has a fastener disposed therein for securing the respective electrode received in the at least one upper connector assembly and the at least one lower connector assembly.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
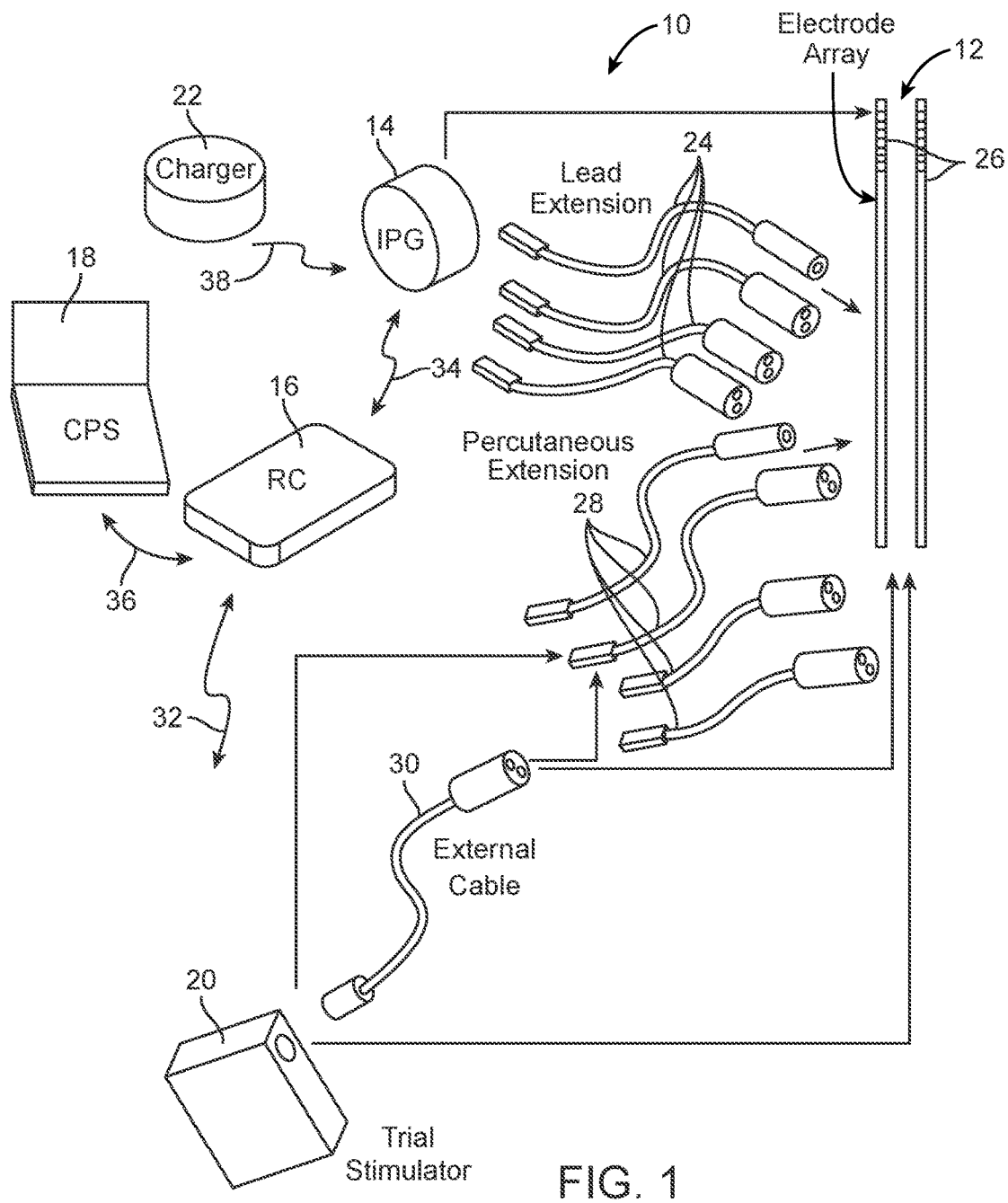
FIG. 1 is a plan view of one embodiment of a neurostimulation system arranged in accordance with the present inventions.

Turning first to FIG. 1, an exemplary SCS system 10 generally includes one or more (in this case, two) implantable neurostimulation leads 12, a neurostimulator (i.e., an implantable pulse generator) (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 24 and external cable 30 to the neurostimulation leads 12. The ETS 20, which has similar pulse generation circuitry as that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided.

The RC 16 may be used to telemetrically control the ETS 20 via a bi-directional inductive link 32. Once the IPG 14 and neurostimulation leads 12 are implanted, the RC 16 may also be used to telemetrically control the IPG 14 via a bi-directional magnetic coupling link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. It should be noted that rather than an IPG, the system 10 may alternatively utilize an implantable receiver-stimulator (not shown) connected to the lead 12. In this case, the power source, e.g., a battery, for powering the implanted receiver, as well as control circuitry to command the receiver-stimulator, will be contained in an external controller/charger inductively coupled to the receiver-stimulator via an electromagnetic link.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link or magnetic coupling link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
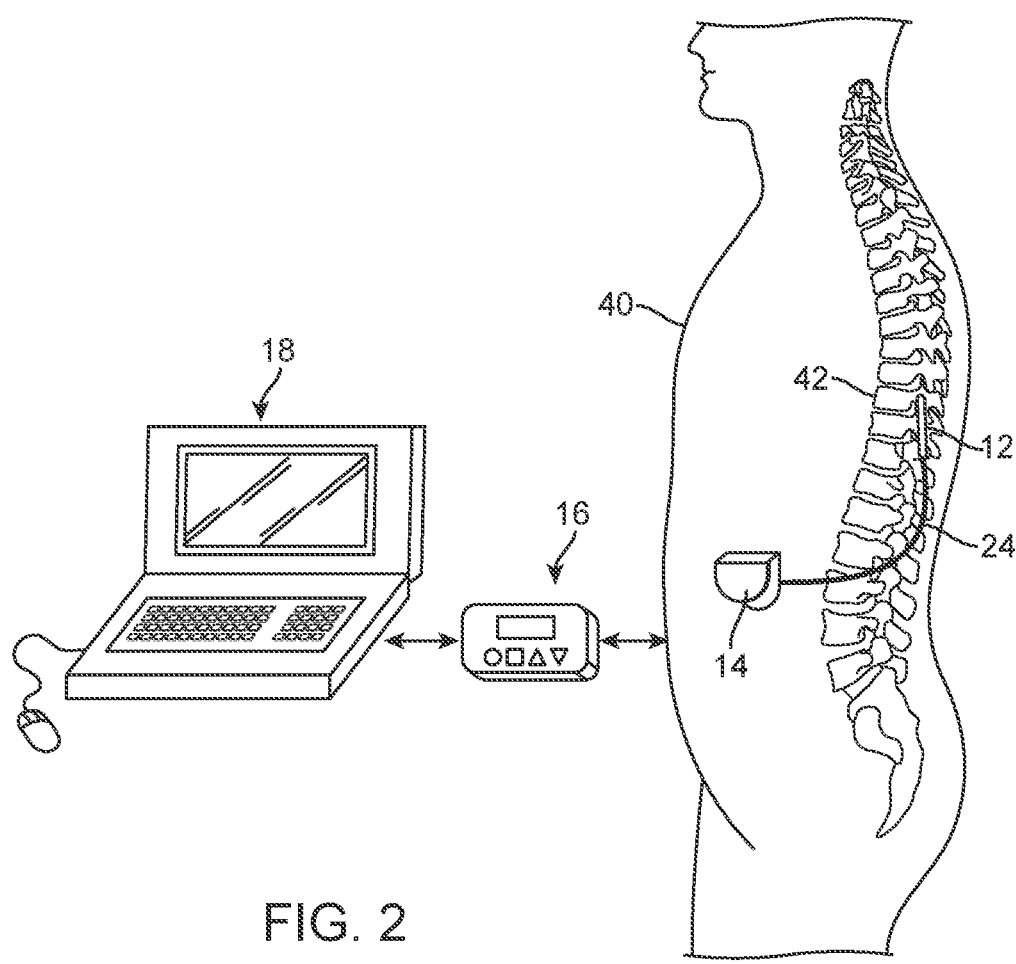
FIG. 2 is a plan view of the neurostimulation system of FIG. 1 in use with a patient.

As shown in FIG. 2, the electrode leads 12 are implanted within the spinal column 42 of a patient 40. The preferred placement of the neurostimulation leads 12 is adjacent, i.e., resting near, or upon the dura, adjacent to the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 3:
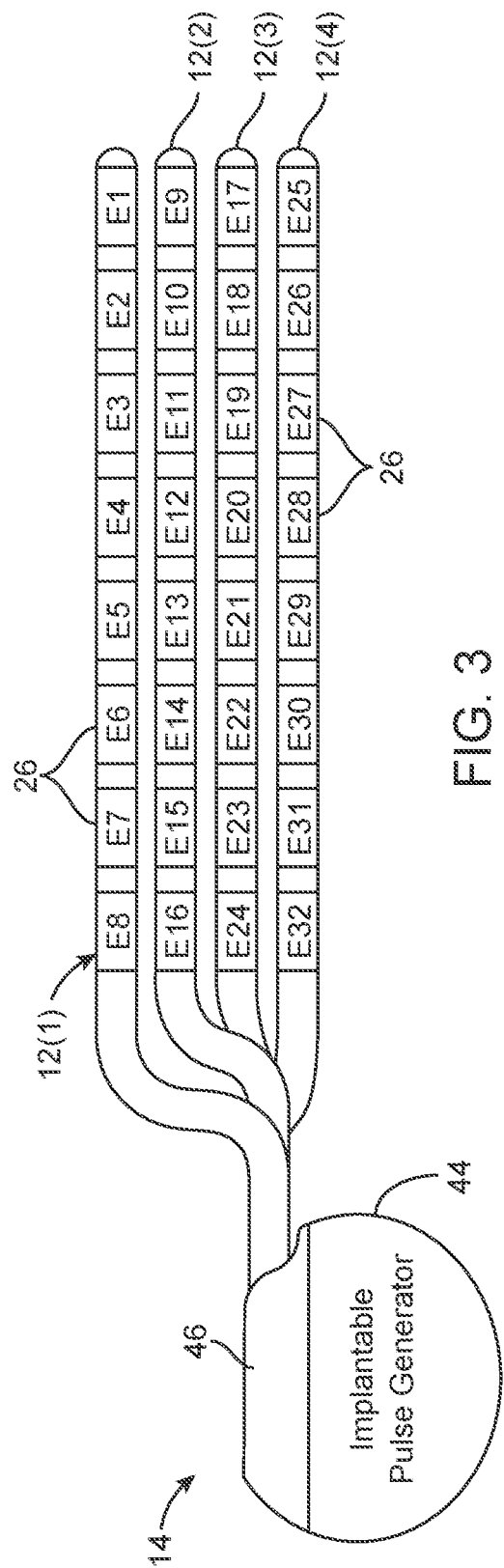
FIG. 3 is a side view of a neurostimulator and electrode leads used in the neurostimulation system of FIG. 1.

Referring now to FIG. 3, the external features of the neurostimulation leads 12 and the IPG 14 will be briefly described. In the illustrated embodiment, there are four stimulation leads 12(1)-12(4), wherein neurostimulation lead 12(1) has eight electrodes 26 (labeled E1-E8), neurostimulation lead 12(2) has eight electrodes 26 (labeled E9-E16), neurostimulation lead 12(3) has eight electrodes 26 (labeled E17-E24), and neurostimulation lead 12(4) has eight electrodes 26 (labeled E24-E32). The actual number and shape of leads and electrodes will, of course, vary according to the intended application.

Figure 4:
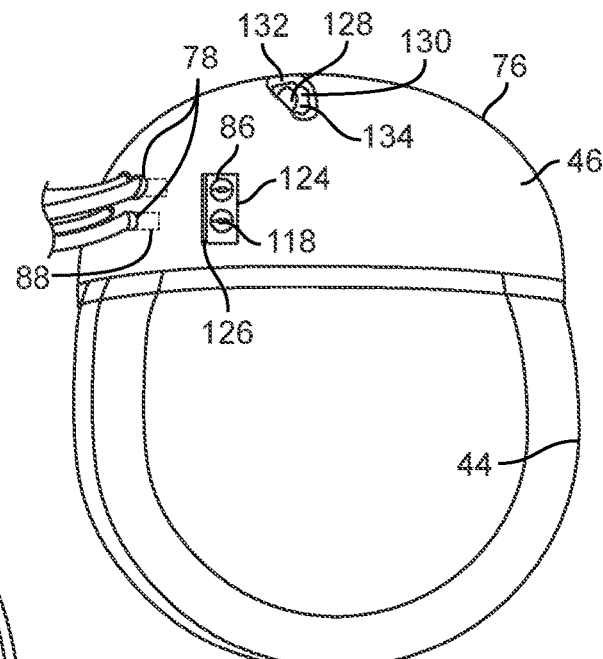
FIG. 4 is a perspective view of the neurostimulator of FIG. 3.

As shown in FIGS. 3 and 4, the IPG 14 comprises an outer case 44 for housing the electronic and other components (described in further detail below), and a header portion 46 coupled to the case 44 for receiving the proximal ends of the neurostimulation leads 12(1)-12(4) for mating in a manner that electrically couples the electrodes 26 to the electronics within the case 44.

The outer case 44 is composed of an electrically conductive, biocompatible material, such as titanium 6-4, and forms a hermetically sealed compartment wherein the internal electronics are protected from the body tissue and fluids. In the illustrated embodiment, the case 44 has a rounded configuration with a maximum circular diameter D of about 50 mm, and preferably about 45 mm, and a maximum thickness W of about 10 mm, and preferably about 8 mm. The case 44 is formed using any suitable process, such as casting, molding, and the like. The header 46 has a rounded configuration that corresponds with that of the case 44, such that the case 44 and the header 46 together form a rounded body.

As will be described in further detail below, the IPG 14 includes pulse generation circuitry 48 (see FIG. 6) that provides electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case 44. Stimulation energy may be transmitted to the tissue in a monopolar or multipolar (e.g., bipolar, tripolar, etc.) fashion. Monopolar stimulation occurs when a selected one of the lead electrodes 26 is activated along with the case 44 of the IPG 14, so that stimulation energy is transmitted between the selected electrode 26 and case 44. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 5:
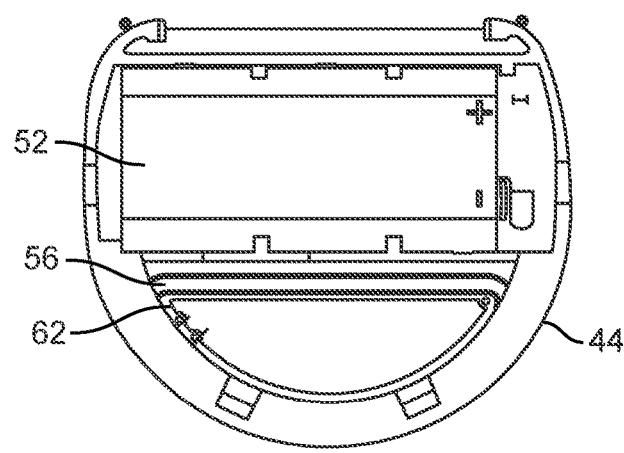
FIGS. 5 and 6 are cut-away views of opposing sides of the neurostimulator of FIG. 3.
Figure 6:
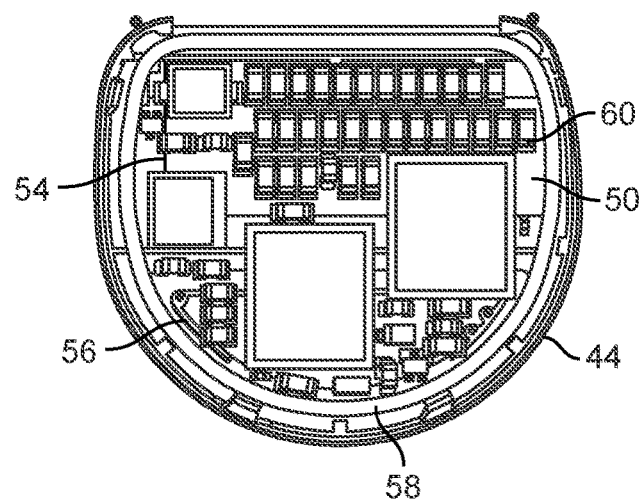
Figure 13A:
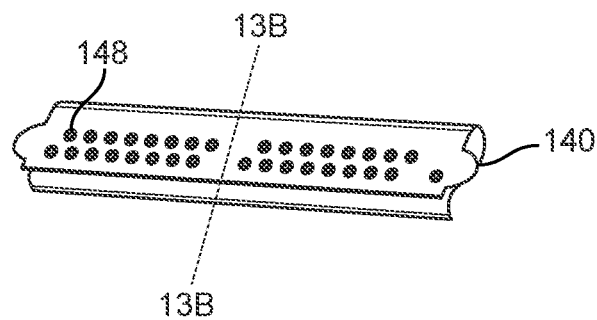
FIG. 13A is a perspective view of a flex circuit having holes for receiving the feedthrough pins from FIGS. 11 and 12.
Figure 13B:
FIG. 13B is a cross-sectional view of the flex circuit in FIG. 13A taken along the line 13B.

Referring to FIGS. 5 and 6 which show opposing internal sides of case 44, in performing the above-described stimulation energy generation function, the IPG 14 comprises multiple electronic components, including an electronic substrate assembly 50 and a battery 52 contained within the case 44, and a flex circuit 140 (see FIGS. 13A and 13B) coupled to the electronic substrate assembly 50. The flex circuit 140 serves to couple the electronic substrate assembly 50 to the electronic components in the header 46, which will be discussed in further detail below. The electronic substrate assembly 50 includes a printed circuit board (PCB) 54 to which the previously described pulse generation circuitry 48 is mounted in the form of microprocessors, integrated circuits, capacitors, and other electronic components. The electronic substrate assembly 50 further comprises a telemetry coil 56, a charging coil 58, and telemetry/charging circuitry 60 mounted to the PCB 54. While a portion of the electronic components of the IPG 14 will be described in further detail below, additional details of the IPG 14 and electrical components are disclosed in U.S. Pat. No. 6,516,227, which was previously incorporated herein.

Figure 7:
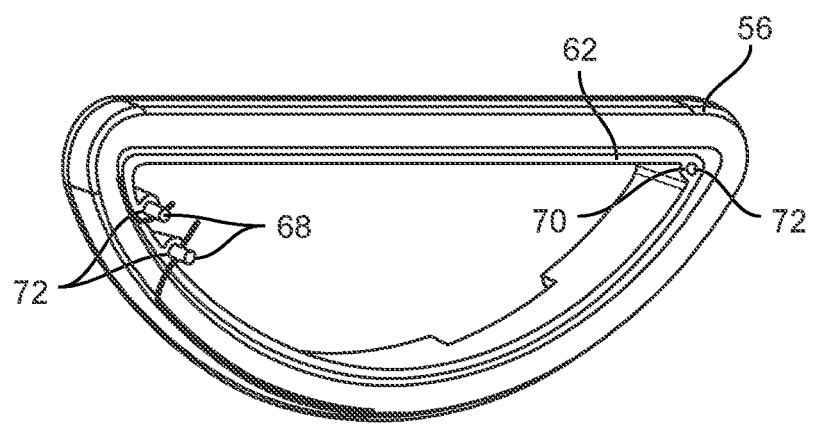
FIG. 7 is a side view of a spacer and telemetry coil from the neurostimulator of FIG. 3.
Figure 8:
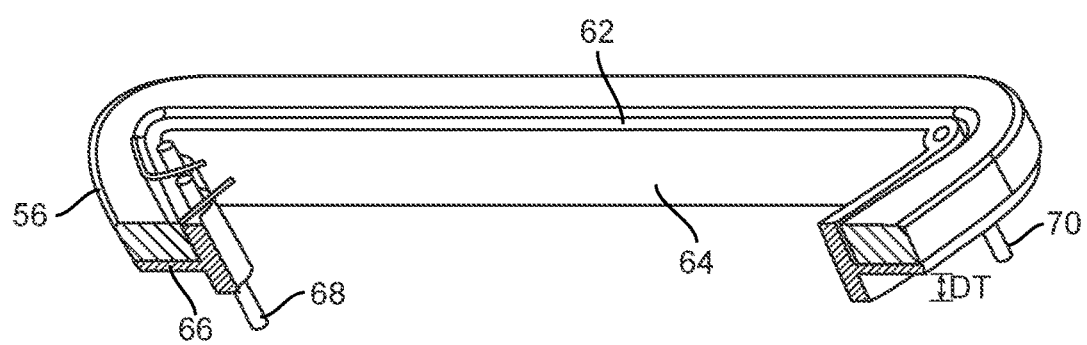
FIG. 8 is a cross-section view of the spacer and telemetry coil of FIG. 7.

The telemetry coil 56 and charging coil 58 are positioned on opposing sides of the PCB 54. Significantly, as shown in FIGS. 7 and 8, the electronic substrate assembly 50 further comprises a spacer 62 on which the telemetry coil 56 is positioned to space the telemetry coil 56 a distance Dt away from the PCB 54. In the illustrated embodiment, the spacer 62 is a bobbin 62. The bobbin 62 has a main body 64 and an outer flange 66 extending around the periphery of the main body 64 on which the telemetry coil 56 sits, such that the coil 56 is wound around the main body 64 in a shape corresponding to that of the main body 64. Here, the telemetry coil 56 and the main body 64 of the bobbin 62 have a D-shaped configuration for encompassing a wide area in the case 44 to improve coupling, and hence the reliability of data transfer, between the telemetry coil 56 and the RC 16. In addition to maintaining the telemetry coil 56 a distance away from the PCB 54, the bobbin 62 is beneficial for manufacture, as the bobbin 62 provides a base on which to shape the telemetry coil 56, creating a more consistent design than freeform winding of the telemetry coil 56.

A number of pins 68, 70 are affixed to the bobbin for coupling the telemetry coil 56 to the PCB 54. In the illustrated embodiment, the bobbin 62 has three holes 72 extending through the main body 64 of the bobbin 62 for receiving three pins 68, 70. In this embodiment, two of the pins 68 electrically connect the telemetry coil 56 to the PCB 54, and in particular, one pin 68 connects the ground port of the telemetry coil 56, and the other pin connects the signal port of the telemetry coil 56. The third pin 70 mechanically connects the telemetry coil 56 to the PCB 54. In the illustrated embodiment, the two holes 72 for receiving the two electrical pins 68 are located on one side of the main body 64 of the bobbin 62, and the one hole 72 for receiving the mechanical pin 70 is located on an opposing side of the main body 64 of the bobbin 62. The pins 68, 70 may be secured in the holes 72 by welding or other suitable means. In this manner, the pins 68, 70 facilitate secure, accurate placement of the telemetry coil 56 relative to the PCB 54, while the two pins 68 also provide an electrical connection between the telemetry coil 56 and the PCB 54. In other embodiments, only one pin may be used to electrically connect the telemetry coil 56 to the PCB 54, or more pins may be used to electrically and/or mechanically connect the telemetry coil 56 to the PCB 54.

Notably, many typical IPGs contain a charging coil in the case and a telemetry coil in the header. In the illustrated embodiment, however, positioning both the charging coil 58 and the telemetry coil 56 in the case 44 allows more room in the header 46 for other electronic components. Additionally, positioning the telemetry coil 56 in the case 44 eliminates the need for a feedthrough that connects the electronic substrate assembly 50 with the telemetry coil 56, as opposed to when a telemetry coil is in the header.

To realize potential effects associated with positioning both the telemetry coil 56 and charging coil 58 in the case, it is helpful to note the operation of the coils 56, 58. Regarding the telemetry coil 56, wireless data telemetry between the RC 16 and the IPG 14 occurs via inductive coupling, for example, magnetic inductive coupling. This coupling occurs between the telemetry coil 56 in the IPG 14 and a corresponding external coil (not shown) in the RC 16. When data is sent from the RC 16 to the IPG 14, the external coil in the RC 16 is energized with an alternating current (AC). This energizing of the external coil to transfer data can occur using a Frequency Shift Keying (FSK) protocol, for example, in which digital data bits in a stream are represented by different frequencies, as disclosed in U.S. patent application Ser. No. 11/780,369, which is incorporated herein by reference. Energizing the external coil with these frequencies produces a magnetic field, which in turn induces a voltage in the telemetry coil 56 in the IPG 14, producing a corresponding current signal when provided a closed loop path. This voltage and/or current signal can then be demodulated to recover the original data. Transmitting data in the reverse, from the telemetry coil 56 to the external coil, occurs in essentially the same manner.

Regarding the charging coil 58, when power is to be transmitted from the external charger 22 to the IPG 14, the charging coil 58 is energized with an alternating current (AC). Such energizing is generally of a constant frequency and may be of a larger magnitude than that used during data transfer with the telemetry coil 56, but the basic operation is similar. The IPG 14 can also communicate back to the external charger 22 by modulating the impedance of the charging coil 58. This change in impedance is reflected back to the external charger 22, which demodulates the reflection to recover the transmitted data. This means of transmitting data from the IPG 14 to the external charger 22 is known as Load Shift Keying (LSK) and is useful to communicate data relevant during charging of the battery 52 in the IPG 14, such as the capacity of the battery 52, extent of charging completed, and other charging variables. LSK communication between an IPG and external charger is further detailed in U.S. patent application Ser. No. 12/354,406, which is incorporated herein by reference.

One possible issue that may arise with positioning both the telemetry coil 56 and the charging coil 58 in the case 44 is that the mutual inductance of the coils 56, 58 may interfere with each other if both coils 56, 58 are receiving and transmitting data at the same time. One method of addressing this is to include decoupling circuitry (not shown) for decoupling the charging coil 58 from the charging circuitry 60 during periods of telemetry between the IPG 14 and the RC 16. The decoupling circuitry may be activated based on one or more operating factors, for example, when the telemetry coil 56 is sending or receiving data to/from the RC 16, or when the charging circuitry 60 detects no charging alternating current for the charging coil 58 to receive.

In another method, the LSK data signal is used to transmit serial data to the external charger 22 during charging, as is typical, and is also used as a control signal to reduce loading of the telemetry coil 56 during data telemetry between the IPG 14 and the RC 16. Using the preexisting LSK circuitry in this method requires no change in telemetry circuitry other than to program the IPG 14 circuitry to assert LSK data during periods of data telemetry. Thus, the enhanced circuitry improves reliability of telemetry between the RC 16 and the telemetry coil 56 without substantial circuitry changes. Additional information regarding the enhanced circuitry is detailed in application Ser. No. 12/616,178, filed Nov. 11, 2009, which is incorporated herein by reference.

The bobbin 62 also provides operational benefits with positioning the telemetry coil 56 and the charging coil 58 in the case 44. For example, the bobbin 62 lessens the interference between the coils 56, 58 by increasing the distance between the telemetry coil 56 and the charging coil 58, as described above. Additionally, the bobbin 62 places the telemetry coil 56 in closer proximity to the case 44 to optimize telemetry using resistance from the case 44. To illustrate, the telemetry coil 56 may communicate on a seven-band frequency that is achieved by attaining a loss in transmission from resistance, e.g., resistance from adjacent material. In prior embodiments wherein the telemetry coil is positioned in the header, the header provides the resistance needed to obtain the ideal frequency. In the present embodiment, in positioning the telemetry coil 56 closer to the case 44, the case 44 provides the resistance needed to create the desired seven-band frequency for telemetry coil 56 transmission.

As mentioned above, the flex circuit 140 serves to couple the electronic substrate assembly 50 to the electronic components in the header 46. In particular, the flex circuit 140 is coupled to the PCB 54 and also to feedthrough pins, described in further detail below, that in turn are coupled to lead extensions 24 received in the header 46. As the flex circuit 140 is a flexible metallic component (see e.g., FIGS. 13A and 13B), the flex circuit 140 serves as an interface between the electronic substrate assembly 50 and the electronic components in the header 46 to provide an electrical coupling function along with the ability to be bent in a suitable configuration to accommodate the size and structure of the IPG 14.

Coupling the flex circuit 140 to the PCB 54 eliminates the need for soldering an additional plate to the PCB 54, making manufacture more efficient and eliminating related quality issues that may otherwise arise. In some embodiments, the flex circuit 140 may be permanently coupled to the PCB 54, for example, by soldering, laser-welding, applying conductive epoxy or similar adhesive, or crimping. In other embodiments, the flex circuit 140 may be detachably coupled to the PCB 54, for example, by edge connectors such as zero insertion force connectors, snap-fit mechanisms, friction-fit mechanisms, and fasteners such as screws. In one embodiment, the substrate of the flex circuit 140 is composed primarily of polyamide, which may be the same material from which the PCB 54 is primarily composed. Other materials may also be used for the substrate of the flex circuit 140.

Figure 9:
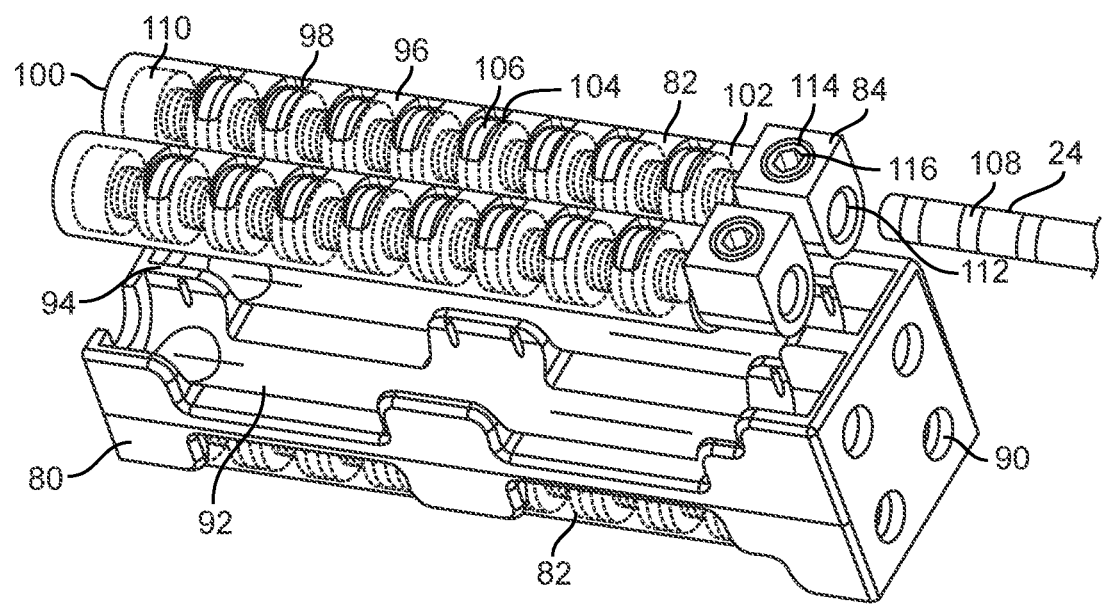
FIGS. 9 and 10 are partial exploded view of connector assemblies in a retainer element from the neurostimulator of FIG. 3.

As mentioned above, the electronic components within the case 44 are electrically coupled to the electrodes 26 via lead extensions 24 received in the header 46, as shown in FIG. 4. Referring to FIGS. 4 and 9, the header 46 includes: a shell 76 coupled to the case 44; a plurality of ports 78; a retainer 80; one or more connector assemblies 82 positioned in the retainer 80; a corresponding number of connector blocks 84 positioned in the retainer 80; one or more septums 86; and a plurality of strain relief members 88.

The shell 76 is formed using any suitable process, such as casting, molding, and the like, and is composed of a rigid material that does not interfere with the electrical functions of the IPG 14, such as thermoset. The plurality of ports 78 extend through the shell 76 and are configured for receiving the lead extensions 24. Preferably, the number of ports 78 corresponds to the number of lead extensions 24. For example, in the illustrated embodiment, there are four lead extensions 24 and four ports 78. The header ports 78 are also aligned with retainer ports 90, such that the lead extensions 24 are received in the header ports 78 and then in the retainer 80 through the retainer ports 90. The retainer ports 90 (in this illustrated embodiment, four ports) are in turn aligned with the connector assemblies 82, such that the lead extensions 24 are received through the retainer ports 90 and then within the connector assemblies 82.

Figure 10:
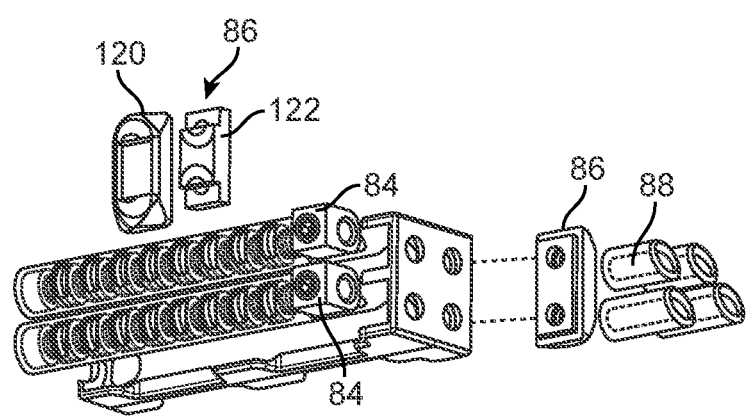

As shown in FIGS. 9 and 10, the retainer 80 receives the connector assemblies 82 in corresponding retainer channels 92 that hold each respective connector assembly 82 in position. The retainer 80 is preferably composed of a rigid material, e.g., thermoplastic, such that the connector assemblies 82 can be affixed relative to each other. In one embodiment, the connector assemblies 82 are releasably disposed in the retainer 80 in a suitable manner, such as with an interference fit, snap connection, binders, or other suitable mechanisms. Partitions 94 in the retainer 80 keep the connector assemblies 82 separated to minimize interference.

The connector assemblies 82 receive and make electrical contact with the lead extensions 24. Each connector assembly 82 has a housing 96, a hollow center region 98 extending between a proximal end 100 and a distal end 102 of the housing 96, a plurality of openings 104 transversely formed through the wall of the housing 96, and a plurality of connector contacts 106 located within the hollow center region 98. In the illustrated embodiment, there are four connector assemblies 82 aligned in a 2×2 configuration to make efficient use of space. Specifically, there are two upper assemblies 82 and two lower assemblies 82, wherein the two lower assemblies 82 are designated as being closer to the case 44 than the two upper assemblies 82. Other embodiments may include one assembly 82, or two assemblies 82 or more arranged in a manner suited to the configuration of the IPG 14. Suitable materials for the housing 96 include, for example, silicone and polyurethane, and multiple materials may be included. Each lead extension 24 is received through the distal end 102 of the respective housing 96 into the respective hollow center region 98.

The openings 104 in the housing 96 extend from an outer surface of the housing 96 to the hollow center region 98. Preferably, the housing openings 104 are linearly aligned along a side surface of the housing 96. Each opening 104 provides access to a corresponding connector contact 106 within the housing 96. The connector contacts 106 are electrically coupled to the electronic substrate assembly 50 in the case 44 by a plurality of feedthrough pins, which are explained below in greater detail.

When the lead extensions 24 are received in the connector assemblies 82, the connector contacts 106 electrically couple with terminals 108 disposed on the lead extensions 24. The terminals 108 are in turn coupled to the lead electrodes 26 with conductive wires (not shown). Preferably, the number and spacing of the connector contacts 106 in each connector assembly 82 correspond to the number and spacing of the terminals 108 on each lead extension 24 to optimize coupling. In the illustrated embodiment, each of the four connector assemblies 82 has eight contacts 106, and each of the four lead extensions 24 has eight terminals 108. In this manner, when a lead extension 24 is received in the hollow center region 98 of the connector assembly 82, each connector contact 106 electrically couples to a corresponding terminal 108 on the lead extension 24. This results in coupling between the electronic substrate assembly 50, which is coupled to the connector contacts 106 by the flex circuit 140 and the feedthrough pins, and the electrodes 26, which are coupled to the terminals 108.

The retainer 80 has a number of end stops 110 each located at the proximal ends 100 of the housings 96 of the connector assemblies 82. The end stops 110 are typically formed of a compressible material, such as silicone, and may be shaped as a block or alternatively have a curved bowl-shaped configuration. The end stops 110 help to set the pitch for placement of the connector contacts 106 during manufacture, for example, during precision-based processes such as laser soldering, to prevent irregular placement of the connector assemblies 82 that would lead to increased expense and quality issues. Also, during operation of the IPG 14, the end stops 110 help limit movement of the connector assemblies 82 to optimize transmission of electrical pulses from the connector assemblies 82 to the lead electrodes 26. Additional details regarding setting of pitch and use of end stops for connector assemblies are further described in U.S. Provisional Patent Application No. 61/378,613, filed Aug. 31, 2010, and U.S. Pat. No. 7,244,150, which are incorporated herein by reference.

The connector blocks 84 are located at the distal end 102 of the housing 96 and may also be coupled to the housing 96 and/or a wall of the retainer 96. In the illustrated embodiment featuring the 2×2 connector assembly configuration, there are two upper connector blocks 84 adjacent the two upper assemblies 82 and two lower connector blocks 84 adjacent the lower assemblies 82. Each connector block 84 defines a port 112 aligned with the hollow center region 98 for receiving a lead extension 24. Each connector block 84 also has an aperture 114 on a side of the connector block 84 through which a fastener 116, such as a setscrew or pin, is inserted and secured against the lead extension 24 received therein. This helps to prevent undesirable detachment of the lead extensions 24 from the IPG 14 and to optimize electrical coupling between the lead terminals 108 and connector contacts 106.

Figure 10A:
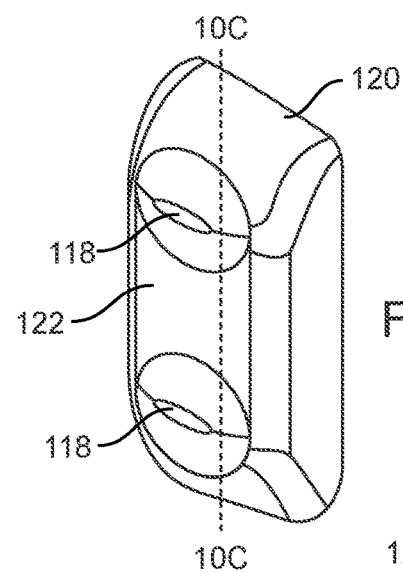
FIG. 10A is a perspective view of a septum featured in FIG. 9.
Figure 10B:
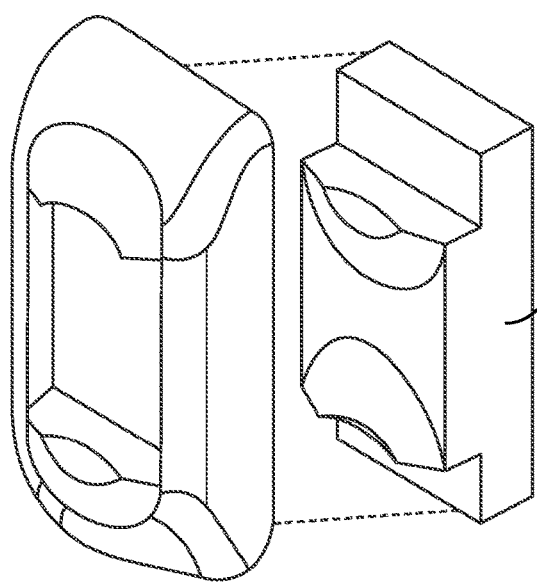
FIG. 10B is an exploded view of the septum of FIG. 10A.
Figure 10C:
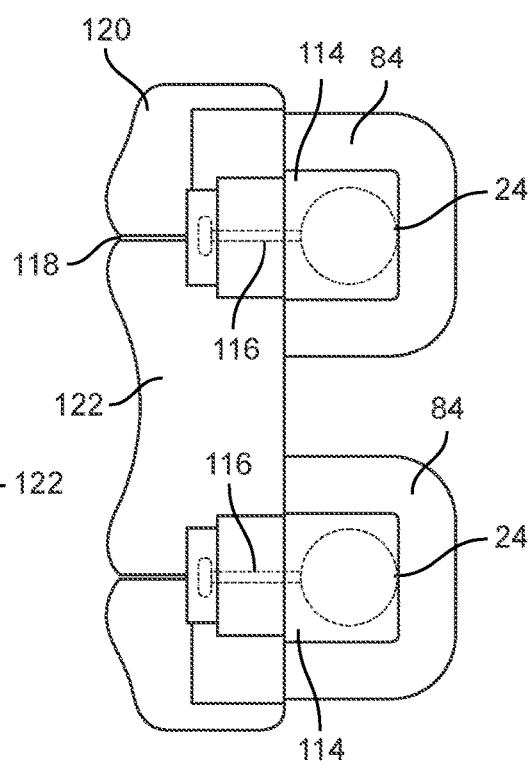
FIG. 10C is a cross-sectional view of the septum of FIG. 10A taken along the line 10C and connector blocks featured in FIG. 9.
Figure 11:
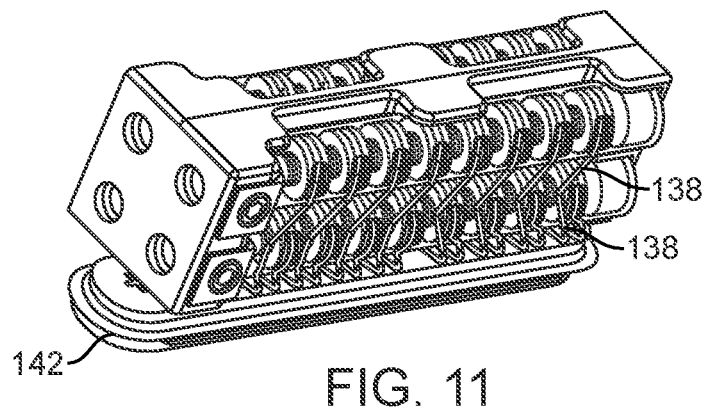
FIG. 11 is a perspective view of feedthrough pins coupled to the connector assemblies from FIG. 9.
Figure 12:
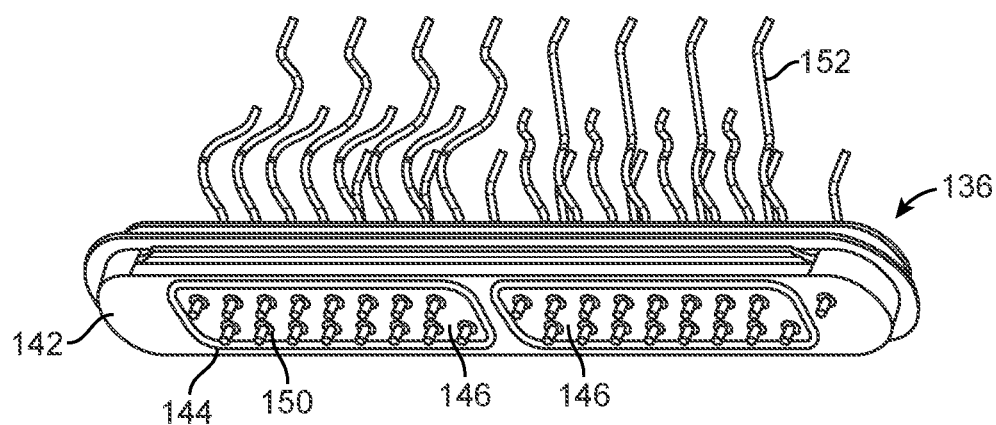
FIG. 12 is a perspective view of a feedthrough assembly with the feedthrough pins from FIG. 11.

The septums 86 have one or more slots 118 aligned with the connector block apertures 114 for receiving a fastening tool to secure the fastener 116 in each aperture 114. The septums 86 are positioned adjacent to, and may also be coupled to, the connector blocks 84. In the illustrated embodiment, two septums 86 are positioned on opposing sides of the header 46, wherein each septum 86 is adjacent to two connector blocks 84. Each septum 86 has an outer block 120 and an inner block 122, as shown in FIG. 10B, wherein the outer block 120 frames the inner block 122, as shown in FIG. 10A. The blocks 120, 122 are composed of a compressible material, such as silicone. The demarcation between the blocks 120, 122 forms the slots 118 for receiving the fastening tool. For example, the upper edge of the inner block 122 forms an upper slot 118 with the outer block 120, and the lower edge of the inner block 122 forms a lower slot 118 with the outer block 120. Additionally, as shown in FIG. 10C, the upper slot 118 in each septum 86 is adjacent to the aperture 114 in each upper connector block 84, and the lower slot 118 in each septum 86 is adjacent to the aperture 114 in the lower connector block 84.

Notably, in other devices wherein a septum only includes one block, the block is typically pierced with a knife to create the slot for receiving the fastening tool. However, this often results in coring of the material, wherein the cored material hinders insertion of the fastener. Additionally, silicone can demonstrate a tendency to "self-heal," such that a slot formed by piercing a silicone block could close at least partially over time. However, by implementing two silicone blocks that are pushed together, as in the illustrated embodiment, the tendency to self-heal is mitigated, and the slot remains intact.

Each septum 86 is positioned in an opening 124 formed through a surface of the header 46 (see FIG. 4), wherein edges of the opening 124 extend over the space underneath to form a frame 126, and the septum 86 is positioned under the frame 126. In typical manufacturing practices, the septum is pushed from outside the header into an opening in the header. However, this often results in the septum becoming loose and being expelled from the header. In the present embodiment, however, the septum 86 is pushed into the opening 124 from inside the header 46, such that the frame 126 edges extending over the opening 124 prevent the septum 86 from moving outside the opening 124. An adhesive, such as epoxy, is also applied to adhere the septum 86 to the header 46, such that both mechanical and adhesive elements hold the septum 86 in place. Additional details regarding the connector assemblies and the components associated therewith are found in U.S. Provisional Patent Application No. 61/378,613, filed Aug. 31, 2010, U.S. Pat. No. 7,244,150, and U.S. patent application Ser. No. 11/532,844, which are incorporated herein by reference.

The strain relief members 88 in the header 46 extend between each of the retainer ports 90 and the header ports 78. In the illustrated embodiment, there are four strain relief members 88 that correspond with the 2×2 configuration of the connector assemblies 82, such that there are two upper and two lower strain relief members 88. The strain relief members 88 are formed as annular seals that help to prevent current leakage outside the header 46 and to hold the lead extensions 24 in position when inserted in the connector assemblies 82 while preventing damage to the lead extensions 24. To correspond with the curved formation of the header 46, the lower strain relief members 88 have a longer length than the upper strain relief members 88. This is because there is more space between the distal end 102 of the lower connector assembly 82 and retainer port 90 and the corresponding header port 78 than between the upper connector assembly 82 and retainer port 90 and the corresponding header port 78.

In the illustrated embodiment, the header 46 also features a suture hole 128 that extends between opposing sides of the header 46. To illustrate, a suture needle can go through suture hole 128 by entering one side of the header 46 and exiting on the other side. A clinician implanting the IPG 14 may thus use a suture needle with the suture hole 128 to affix the IPG 14 to bodily tissue to help hold the IPG 14 in place. Each side of the suture hole 128 is surrounded by a divot 130 in an outer surface of the header 46. The divot 130 is cut into the outer surface of the header 46 and has a plurality of side surfaces 132, each side surface 132 preferably angled less than 90 degrees from the outer surface of the header 46, and a bottom surface 134 where the suture hole 128 is positioned. The divot 130 and its configuration allow for ease in accessing the header 46 with a suture needle, particularly a curved suture needle, to affix the IPG 14 to bodily tissue.

Referring to FIGS. 11-13B, a feedthrough assembly 136 electrically couples the electronic substrate assembly 50 with the connector assemblies 82. The feedthrough assembly 136 includes a plurality of feedthrough pins 138, a metal flange 142 defining a well 144, and one or more ceramic plates 146 positioned in the well 144.

The feedthrough pins 138 are formed of 10 mL wire composed of 90/10 platinum/iridium. In other feedthrough assemblies, the pins are composed of 80/20 platinum/iridium, however, this is less ductile and less compatible with soldering processes during manufacture. Preferably, the number of feedthrough pins 138 corresponds to the number of connector contacts 106 in the connector assemblies 82. In the illustrated embodiment, there are thirty-two feedthrough pins 138. The feedthrough pins 138 are coupled to the PCB 54 and extend through the case 44 and header 46 to the connector assemblies 82, where the pins 138 are coupled to the connector contacts 106. The feedthrough pins 138 may be coupled to the connector contacts 106 by any suitable method including, for example, welding, soldering, and the like. Notably, the feedthrough pins 138 are sufficiently long to reach the connector contacts 106 without requiring an additional wire to be soldered to each pin 136. This eliminates the need for additional manufacturing steps, thus limiting production costs and quality issues that would otherwise arise.

As mentioned above, the feedthrough pins 138 are each coupled to the flex circuit 140, which may be achieved in various manners. In the illustrated embodiment, each of the feedthrough pins 138 is inserted in a corresponding hole 148 in the flex circuit 140 (see FIG. 13A). To insert the feedthrough pins 138 through the flex circuit 140 during manufacture, the flex circuit 140 is initially flat, wherein each of the feedthrough pins 138 is inserted through the corresponding hole 148. Using laser soldering, gold braze is applied on the underside of each hole 148 around each pin 138 and seeps through the holes 148 to seal the pins 138 in the holes 148. This provides a metallurgical adhesive and electrical connection, which may be advantageous over other sealants that only serve as an adhesive. Conductive epoxy may also be used to seal the pins 138 in the holes 148. The flex circuit 140 is then bent into a curved configuration to suitably fit in the IPG 14 and to orient the pins 138 upward for insertion through the header 46.

In another embodiment, the feedthrough pins 138 are attached to an edge of the flex circuit 140, for example, by laser-soldering or with a conductive epoxy. In another embodiment, a portion of the pins 138 are attached to an edge of the flex circuit 140, and the remaining pins are inserted through holes 148 in the flex circuit 140.

In entering the header 46, the feedthrough pins 138 extend through the metal flange 142, which is located at the base of the header 46. The metal flange 142 is composed of a biocompatible material, such as titanium. As mentioned above, the metal flange 142 defines the well 144, which is occupied by the ceramic plates 146. The ceramic plates 146 are fused to the metal flange 142 with gold braze. In the illustrated embodiment, two ceramic plates 146 are positioned adjacent each other in the well 144. Alternative embodiments may consist of only one ceramic plate 146 that occupies the well 144. The ceramic plates 146 have a number of holes 150 corresponding to the number of feedthrough pins 138, such that each pin 138 extends through one corresponding hole 150. The pins 138 are fused to the ceramic plates 146 with gold braze that is applied on the underside of the plates 146 and seeps through the holes 150 to cover the pins 138 along the length of the holes 150.

The ceramic plates 146 have a lower coefficient of expansion than the titanium of the metal flange 142, such that when the components are heated to extremely high temperatures during manufacture, the ceramic plates 146 expand less than the flange 142. As a result, less of the gold braze can seep from between the metal flange 142 and the ceramic plates 146. Also, since the holes 150 receiving the pins 138 in the plates 146 do not widen significantly, the gold braze securing the pins 138 is substantially prevented from seeping through the holes 150, thus serving to stabilize the pins 138.

To isolate the feedthrough pins 138 from each other and limit electrical connectivity in between, and to further provide protection to the pins 138 in the transition between the case 44 and the header 46, each of the feedthrough pins 138 is covered with a silicone tube 152 from the base of the ceramic plates 146 up to the point at which the feedthrough pins 138 couple to the connector contacts 106 (see FIG. 5). Additionally, the well 144 is filled with silicone (not shown) to provide further isolation between the pins 138.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An implantable medical device, comprising:
   a case that contains circuitry that is configured to deliver electrical stimulation to a patient's tissue;
   a header coupled to the case; and
   a feedthrough assembly positioned between the case and the header, wherein the feedthrough assembly comprises a flange that defines a well, and wherein a plurality of ceramic plates are positioned within the well.

2. The implantable medical device of claim 1, wherein each of the ceramic plates is fused to the flange.

3. The implantable medical device of claim 2, wherein each of the ceramic plates is fused to the flange with gold braze.

4. The implantable medical device of claim 1, wherein each of the ceramic plates comprises a plurality of holes.

5. The implantable medical device of claim 4, wherein the feedthrough assembly further comprises a plurality of feedthrough pins that each extend through one of the holes.

6. The implantable medical device of claim 5, wherein each feedthrough pin is fused to one of the ceramic plates at the hole through which the feedthrough pin extends.

7. The implantable medical device of claim 5, wherein the header comprises one or more connector assemblies that are each configured to receive a stimulation lead that has a plurality of electrodes.

8. The implantable medical device of claim 7, wherein each of the connector assemblies comprises a plurality of connector contacts.

9. The implantable medical device of claim 8, wherein the feedthrough pins connect the circuitry to the connector contacts.

10. The implantable medical device of claim 9, wherein the feedthrough pins are coupled to a flex circuit that is positioned in the case.

11. The implantable medical device of claim 10, wherein the circuitry is mounted on a printed circuit board, and wherein the flex circuit is coupled to the printed circuit board.

12. A feedthrough assembly, comprising:
a metallic flange that defines a well;
a plurality of ceramic plates that are coupled to the flange within the well; and
a plurality of feedthrough pins that each extend through one of a plurality of holes in the ceramic plates.

13. The feedthrough assembly of claim 12, wherein the well is filled with silicone.

14. The feedthrough assembly of claim 12, wherein the ceramic plates are coupled to the flange with gold braze.

15. The feedthrough assembly of claim 12, wherein each feedthrough pin is fused to one of the ceramic plates at the hole through which the feedthrough pin extends.

16. The feedthrough assembly of claim 12, wherein the flange is coupleable to a case of an implantable medical device.

17. The feedthrough assembly of claim 12, wherein the feedthrough assembly is positioned within a header of an implantable medical device.

18. The feedthrough assembly of claim 17, wherein the header comprises one or more connector assemblies that are each configured to receive a stimulation lead that has a plurality of electrodes.

19. The feedthrough assembly of claim 18, wherein each of the connector assemblies comprises a plurality of connector contacts.

20. The feedthrough assembly of claim 19, wherein the feedthrough pins connect circuitry within the implantable medical device to the connector contacts.

* * * * *